Figure 1:
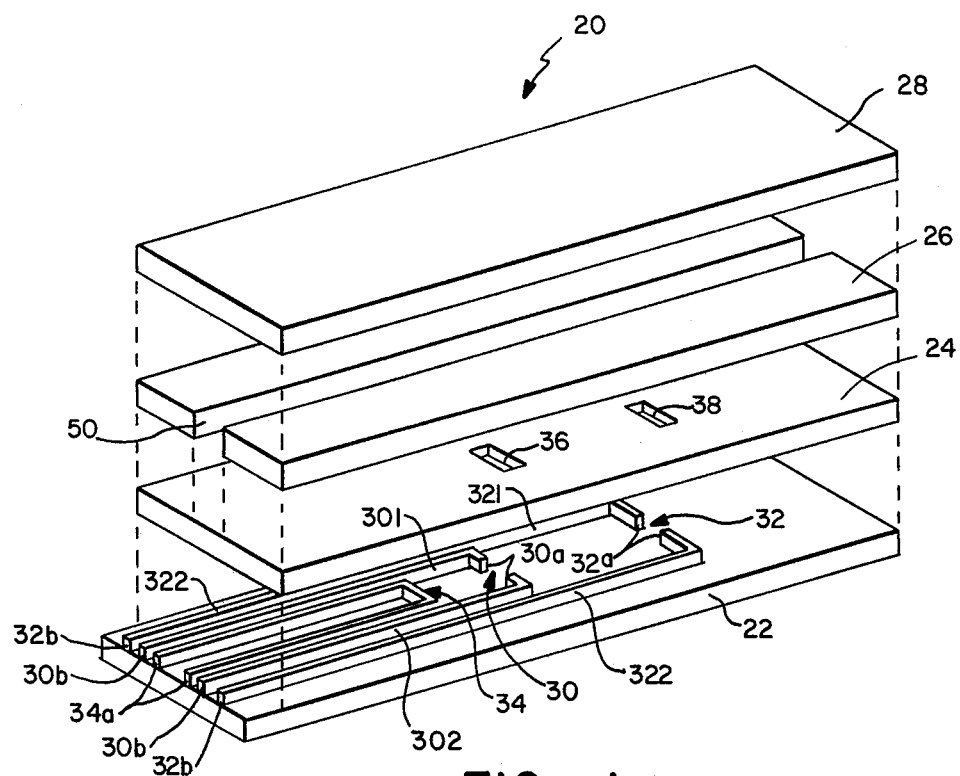

United States Patent [19]

Rhines et al.

[11] 4,339,719
[45] Jul. 13, 1982

[54] CONDUCTIVITY SENSOR FOR MONITORING CORRODENTS BEING DEPOSITED IN A STEAM TURBINE

[75] Inventors: Archie E. Rhines; Steven B. Hugg, both of San Antonio, Tex.

[73] Assignee: Electric Power Research Institute, Inc., Palo Alto, Calif.

[21] Appl. No.: 173,679

[22] Filed: Jul. 30, 1980

[51] Int. Cl.³ .............................. G01N 27/42
[52] U.S. Cl. ................. 324/446; 324/65 CR; 338/27; 338/28; 338/222
[58] Field of Search ............. 324/65 R, 65 CR, 446, 324/450; 338/27, 28, 80, 222

[56] References Cited

U.S. PATENT DOCUMENTS

| | | | |
|---|---|---|---|
| 3,508,148 | 4/1970 | Enfield | 324/446 |
| 3,710,237 | 1/1973 | Watson | 324/446 |
| 3,857,094 | 12/1974 | Caldecourt | 324/65 CR |
| 4,137,495 | 1/1979 | Brown | 324/446 |

*Primary Examiner*—Michael J. Tokar
*Attorney, Agent, or Firm*—Flehr, Hohbach, Test, Albritton & Herbert

[57] ABSTRACT

A conductivity sensor for use in a steam turbine in operation to monitor corrodents being deposited therein. The sensor comprises a bottom substrate on which an electrode pair is located. The bottom substrate also includes a means for measuring the temperature at the bottom substrate. A first layer of dielectric material is bonded to the top of the bottom substrate. The first layer has an aperture formed therein so that an end of the electrode pair is located in the aperture. A second layer of dielectric material is bonded to the top of the first layer. The second layer defines a crevice for entrapping steam-transported corrodents that are deposited in the turbine. A portion of the bottom of the crevice includes the aperture so that corrodents are also deposited in the aperture. By passing a current between the ends of the electrodes located in the aperture, a measure of the conductivity and thus the concentration of corrodents deposited in the aperture and crevice is given. A top substrate is bonded to the top of the second layer of dielectric material to close the crevice. The sensor is constructed so it can be used in an operating turbine.

34 Claims, 3 Drawing Figures

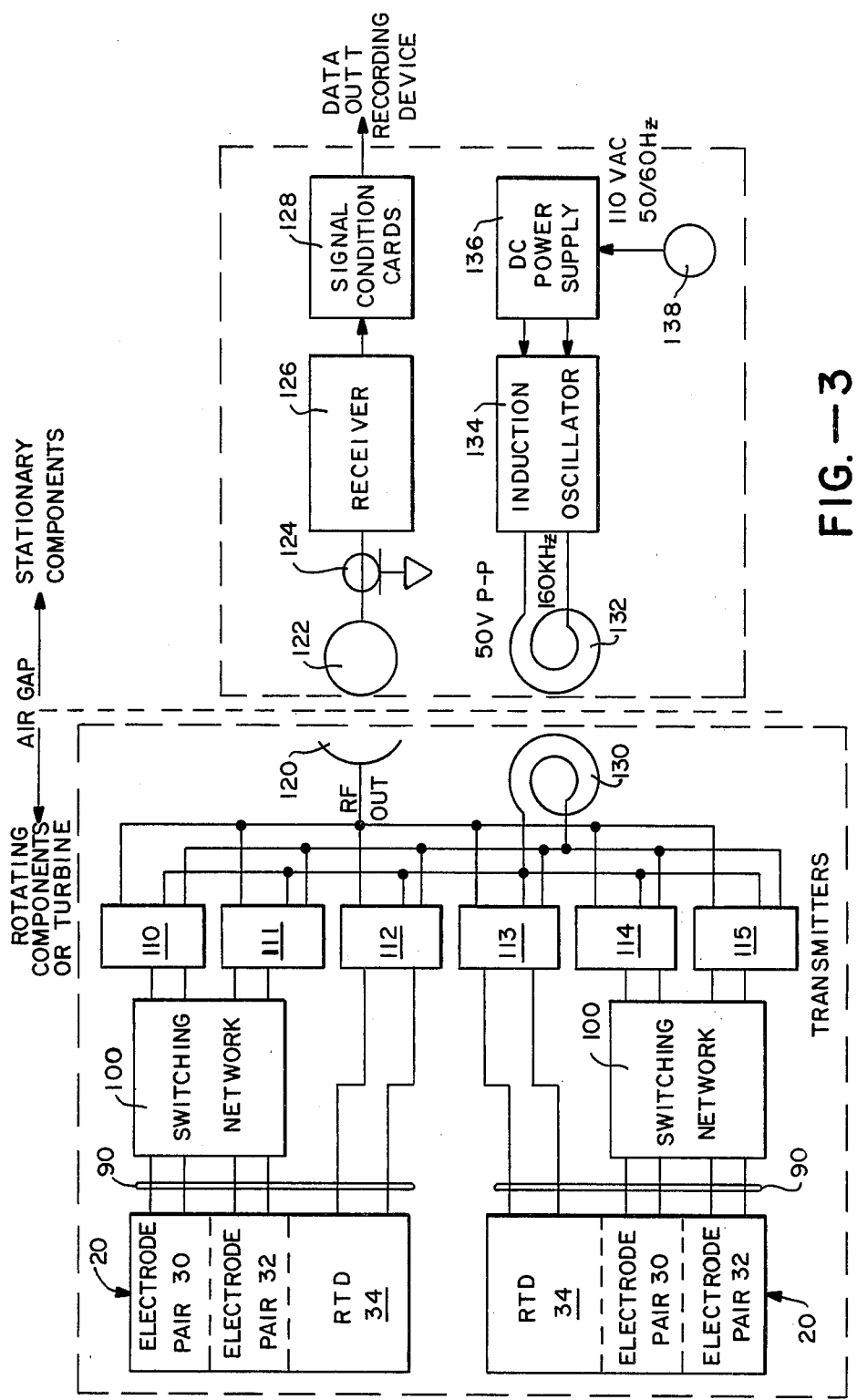
FIG.—3

CONDUCTIVITY SENSOR FOR MONITORING CORRODENTS BEING DEPOSITED IN A STEAM TURBINE

The present invention relates generally to systems for steam-purity monitoring in steam operated power plants, and more particularly, to a conductivity sensor for use in a steam turbine to monitor steam-transported corrodents that are being deposited in the turbine during operation.

Corrosion induced in turbines by steam-transported corrosive impurities is a serious problem in the electrical power industry. As the steam passes through the turbine, corrodents are deposited in the turbine to attack turbine blades and other internal mechanisms. For instance, corrodents present in a transgranular crack in a blade can cause high cycle fatigue of the blade. The corrosion problem has been experienced in units that vary in type from low pressure turbines operating at a pressure of 1000 psig to units with super-critical once-through steam generators.

In an attempt to limit the turbine-corrosion problem, guidelines have been established as to recommended levels of steam purity. Power plant operators have accordingly had to develop new instrumentation and procedures for monitoring steam purity to assure operation within the recommended limits. For example, a continuous analyzer has been developed to monitor, among other things, pH, cation conductivity, and specific conductivity of the steam flowing in the plant water/steam cycle. See Peterson S. H., Bellows J. C., Pensenstadler D. F., and W. M Hickam, "Steam Purity Monitoring for Turbine Corrosion Control: A Total Plant Survey", paper given at the 40th International Water Conference, 1979. The present invention is directed to yet another type of instrument for monitoring corrodents deposited in a steam turbine.

Specifically, the present invention is directed to a sensor that is used to measure conductivity at certain points within the turbine. The sensor is positioned at predetermined locations within the turbine, for example at the turbine rotor keyways, to monitor the concentration of corrodents deposited in the turbine. The sensor is designed to operate in the high temperature, high pressure and high rotational force environment of the operating turbine.

The sensor is particularly adapted to monitor the corrodents deposited at a turbine blade during operation of the turbine. To this purpose, the sensor includes a trap which forms a simulated crevice on the blade to capture steam-transported corrodents. By measuring the conductivity of the solution or material within the trap, the extent of the buildup of corrosive products on the blade is known. This follows from the fact that the corrosiveness of the solution in the trap is directly proportional to its chemical ionic content. Therefore, a higher ionic content means a higher measure of conductivity in the trap. And the higher the measure of conductivity, the greater is the buildup of corrodents in the turbine.

One object of the present invention is to provide real-time monitoring of corrodents being deposited within a turbine during operation.

A more specific object of the present invention is to provide a conductivity sensor for monitoring corrodent buildup, the sensor being able to withstand the high temperatures, high pressures, and high rotational forces associated with an operating turbine.

The conductivity sensor of the present invention is constructed to have a bottom substrate on which an electrode pair is located. As the conductivity measurement is also a function of temperature, a means for measuring the temperature at the bottom substrate is also located at the bottom substrate. A first layer of dielectric material is joined to the top of the bottom substrate. This layer of dielectric material separates and electrically insulates the electrodes of the electrode pair and the temperature measuring means from each other. This layer also has an opening or aperture formed therein so that an end of the electrode pair will be located in the aperture. A second layer of dielectric material defining a crevice is joined to the top of the first layer. The crevice forms a trap for capturing steam-transported corrodents. A portion of the bottom of the crevice includes the aperture of the first layer of dielectric so that corrodents are also deposited in the aperture. By passing a current between the ends of the electrodes located in the aperture, a measure of the conductivity and thus the concentration of corrodents deposited in the aperture and crevice is given. This will give an indication of the extent of the corrosive products being deposited in the turbine during operation. A top substrate is formed on top of the second layer of dielectric to close the top of the crevice. The sensor is able to operate in the turbine's high temperature, high pressure, and large rotational force environment.

Figure 2:
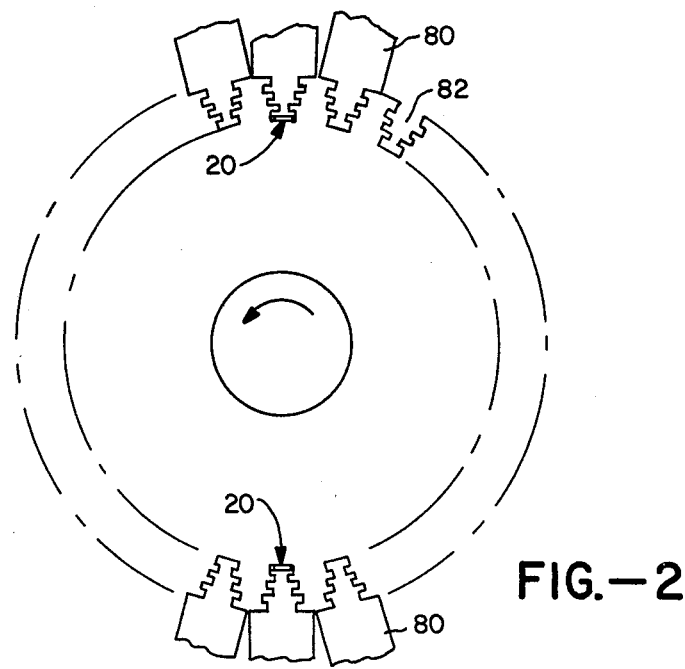

The conductivity sensor of the present invention will be described in more detail hereinafter in conjunction with the drawings wherein:

FIG. 1 is a perspective view illustrating the different elements of the sensor of the present invention;

FIG. 2 diagramatically illustrates an arrangement of two sensors on a turbine blade; and FIG. 3 is a schematic view which shows the switching and telemetry systems used in powering and receiving signals from the sensors of FIG. 2.

Referring now to the drawings, attention is first directed to FIG. 1 which shows conductivity sensor 20 of the present invention. Sensor 20 comprises a bottom substrate 22, a measuring-window dielectric 24, a crevice-spacer dielectric 26, and a top substrate 28. The top and bottom substrates and the two dielectric layers 24 and 26 are constructed of a material that is able to withstand the high temperatures and high pressures present in an operating turbine. The top and bottom substrates are preferably made of alumina, and particularly they may be made from Alsimag 614 manufactured by American Lava. The dielectric layers are made of a ceramic dielectric coating material such as Product No. 4747, Type Vitreous-Crossover, manufactured by Electro-Sciences.

As shown, each of the above elements of the sensor has a rectangular shape with the top substrate and the two dielectric layers being of equal length. The bottom substrate is longer than the other three elements of the sensor. This provides a space for a number of terminals, as will be discussed below, at one end of the bottom substrate. The geometric shape of the substrates and dielectric layers may of course be other than rectangular; for example, they may be square or oval in shape. The sensor may be constructed to have an overall length of about one inch and a height of approximately 0.025 of an inch.

Electrodes 301 and 302 of opposite polarity form a first electrode pair 30 on the top of substrate 22. The electrodes are spaced from one another and electrically insulated from each other so that a current will flow between the electrodes across end 30a of the electrode pair. The opposite ends of the electrodes, which is end 30b of this electrode pair, extend to the end of the bottom substrate to form terminals for the connection of a signal cable 90, see FIG. 3, to the electrodes. As a back-up and/or as a means for obtaining additional data, a second electrode pair 32 may be located on substrate 22. Like electrode pair 30, the electrodes 321 and 322 of electrode pair 32 are spaced apart and electrically insulated from one another. A current will flow between the electrodes only at end 32a of the electrode pair. The opposite end 32b of electrode pair 32 forms the appropriate terminals for connection to the signal cable.

Also located on the bottom substrate is a resistive thermal device (hereinafter RTD) 34. The RTD is used to measure the temperature at the bottom substrate. The RTD is preferably formed, as discussed below, by a suitable conductive path so that the electrical resistance through the path may be measured to determine the temperature at the substrate. The RTD also has appropriate terminals as at 34a for connection to the signal cable. The RTD will be electrically insulated from the electrodes.

As is known in the art, an electrode pair and the RTD may be formed by silk-screening a platinum-gold paste, such as Type 5800B, Thixotrotic paste manufactured by Electro-Science Laboratories Incorporated onto the top of substrate 22 to define appropriate conductor paths. Thereafter, the conductor paths will be thermally fused to substrate 22 by heating the substrate at a temperature of about 950° C. for approximately 45 minutes.

The dielectric layer 24 in silk-screened or formed by any other appropriate means to have at least one aperture or opening 36 formed therein. If two electrode pairs are used as illustrated, a second aperture or measuring window 38 will be formed in layer 24. In any event, assuming two electrode pairs are used, the apertures are located in layer 24 so that when the layer is bonded to substrate 22, the end 30a of electrode pair 30 is located in aperture 36 and the end 32a of electrode pair 32 is located in aperture 38. Dielectric layer 24 is formed by bonding or thermally fusing, as is known, the dielectric material to the top of substrate 22 by heating the dielectric and substrate at a temperature of about 900° C. for approximately 45 minutes. When layer 24 is joined to substrate 22, the dielectric material of layer 24 provides the necessary electrical insulation between the conductor paths of the electrodes and the RTD conductor path.

Another layer 26 of the dielectric material is joined to the top of dielectric layer 24. This layer has a suitable crevice or slot 50 formed therein for the flow of steam therethrough. Appropriate silk-screening operations will be carried out so that the crevice 50 is formed in layer 26. In this regards, the crevice in layer 26 may be formed in any number of ways. For example, as illustrated, multiple screening may be carried out to build up the thickness of layer 26 so that it essentially comprises two rectangular-shaped members spaced apart to form crevice 50. The crevice will preferably extend lengthwise or longitudinally of layer 26 so as to permit the flow of steam from one end of layer 26 to the opposite end. In any configuration of layer 26 though, the bottom of crevice 50 will always include the aperture or apertures of layer 24. In this manner, the corrodents in the steam passing through crevice 50 will not only be deposited in the crevice but also in the apertures. Thus, the conductivity of the corrodent solution deposited in the apertures can be measured by passing an electric current between the ends 30a and 32a of the electrode pairs located in the respective apertures.

To bond layer 26 to layer 24, the components of the sensor so far constructed are fired in an oven, at a temperature of approximately 900° C. for about 45 minutes. This will thermally fuse layers 24 and 26. The top substrate 28 is then bonded to the top of layer 26 to close the crevice. This is done by firing the sensor in an oven at a temperature of about 850° C. for approximately 45 minutes.

In operation, as shown in FIG. 2, two sensors 20 of the present invention are arranged in the turbine to measure corrosive products being deposited. Of course, only one or more than two sensors may be located in the turbine. Particularly, the sensors are located 180° apart to be suitably affixed in the keyways 82 of the turbine blades 80. With the sensors installed as shown, crevice 50 will be parallel to the axis of rotation of the blade and parallel to the steam flow through the turbine. During turbine operation, corrodents in solution will propagate through crevice 50 to collect in the crevice and the apertures 36 and 38 in dielectric layer 24. At such time when the solution evaporates, as when the turbine is shut down, the corrodents will remain within the apertures and the crevice area. When the turbine is again started up, this process will repeat itself. Corrosive products will thus continue to build up in the apertures and crevice. When the turbine is taken out of operation, the sensors may be removed and the corrosive products deposited in the sensor analyzed.

To obtain a measure of corrodents within crevice 50 and thus within the turbine, the conductivity of the material or solution deposited in crevice 50 and the apertures is measured. This is done by passing an electric current across that end of the electrode pair located in the aperture of dielectric layer 24. As shown in FIG. 1, two electrode pairs are provided and as such an electric current is passed between ends 30a and 32a of the electrode pairs located in apertures 36 and 38, respectively. As explained heretofore, an increase in corrodents in the apertures means an increase in the ionic content of the entrapped solution. And this means an increase in the conductivity measured in the apertures. In this manner, the sensor gives an indication of the corrosive problem in the turbine.

As conductivity is also a function of temperature, RTD 34 is mounted on the bottom substrate to measure temperature, the temperature at the bottom substrate being the same as that at the apertures. As is known to one skilled in the art, using the results of laboratory calibrations of the sensors for entrapped solutions with known concentrates of corrodents and at a given range of temperatures, the contribution of temperature of the conductivity measurement may be determined. By using the RTD to measure the temperature at apertures 36 and 38, the conductivity measurement is corrected to provide a true value for corrodent concentration in the crevice.

To supply power and to receive signals from the sensors located on the turbine blade during operation of the turbine, a standard telemetry system is used. One such system is shown schematically in FIG. 3. Also shown are switching networks 100. The switching networks are standard electronic switches, such as a Differential Input Driver with n-channel J-FETC for Switching Applications, Part No. DG145AL, manufactured by Siliconix. The switches are used to alternate the polarity of the respective electrodes of the electrode pairs to prevent electrolysis effects that would otherwise cause decay of the electrodes.

As shown in FIG. 3, appropriate signal wires 90 connect the terminals 30b and 32b of the respective electrode pairs to their respective switching networks. Similarly, signal wires will be extended from the terminals 34a of the RTD to respective transmitters 112 and 113. To make these connections at the terminal base, a high temperature solder is used. A high temperature epoxy may also be added to provide additional mechanical strength at the terminal connections.

Power to the sensor is provided from a suitable alternating current source 138 which is converted to DC power by a DC power supply 136. The DC voltage produced by power supply 136 powers a standard induction oscillator 134. The induction oscillator supplies a 160 KHz signal to a stationary power induction coil 132. The power signal, which is 50 volts peak-to-peak, is then telemetered to a rotating induction coil 130 located on a rotating component of the turbine. The power is thereafter fed through respective transmitters 110 through 115 to switching networks 100 and to the RTD. The transmitters provide the means for transmitting power to the sensors and the means for transmitting data from the sensors. A type of transmitter that may be used is the Wireless Data Coupling Static Strain Transmitter, Model No. 206A, manufactured by Acurex Autodata.

Signals from the electrode pairs and the RTD of the sensors are also fed through the respective transmitters to a transmitting RF antenna 120. Signals are received by a receiving RF antenna 122 and passed through a ground loop 124 to a wireless data coupling receiver 126. Receiver 126, which may be the Wireless Data Coupling Receiver, Model No. 155K, manufactured by Acurex Autodata, produces an analog output that is directly proportional to the conductivity of the solution in the aperture areas in which the ends 30a and 32a of the electrode pairs are located. The receiver also provides an analog output that is directly proportional to the resistance measured by the RTDs; this gives a measure of the temperature at the aperture and thus the temperature of the material entrapped by the sensors. Appropriate signal conditioning cards 128 will be plugged into the receiver to provide gain and balance controls for setting full scale, zero, and range of operation. From the receiver, the signals are fed to any suitable recording device, such as meters, where appropriate calculations can be made to determine the conductivity of the entrapped solution by comparing the temperature readings of the RTDs and the conductivity measured in the sensors' apertures. In this manner, real-time monitoring of conductivity and thus the concentration of the corrodents in the turbine is provided.

Although specific embodiments of the invention have been described herein in detail, the invention is not to be limited to only such embodiments, but rather only by the appendant claims.

What is claimed is:

1. A conductivity sensor for use in a steam turbine in operation to monitor corrodents deposited therein, comprising:
   a top substrate;
   a first dielectric layer joined to the bottom of said top substrate, said first dielectric layer defining a crevice to entrap corrodents;
   a second dielectric layer joined to the bottom of said first dielectric layer, said second dielectric layer having an aperture formed therein to define an opening at the bottom of said crevice;
   a bottom substrate joined to the bottom of said second dielectric layer;
   means for measuring the temperature at said bottom substrate; and
   an electrode pair located on the top of said bottom substrate, an end of said electrode pair located in said aperture to pass a current therethrough to measure the conductivity of the corrodents therein.

2. The sensor of claim 1 wherein said top and bottom substrates are constructed of alumina.

3. The sensor of claim 2 wherein said electrode pair is defined by a platinum-gold conductor path.

4. The sensor of claim 3 wherein said temperature measuring means is defined by a platinum-gold conductor path on said bottom substrate.

5. The sensor of claim 4 including terminal means located on said bottom substrate for connecting said electrode pair and said temperature measuring means to a means for receiving signals therefrom and to a source of electrical power.

6. The sensor of claim 5 in which said electrode pair is connected to a switching means for alternately reversing the polarity of the electrodes of said electrode pair.

7. The sensor of claim 6 in which a telemetry system is used to transmit power to and receive signals from said electrode pair and said temperature measuring means.

8. A conductivity sensor for use in a steam turbine in operation to monitor steam-transported corrodents deposited therein, comprising:
   a top substrate;
   a first dielectric layer defining a crevice for entrapping corrodents and bonded to the bottom of said top substrate to close the top of said crevice;
   a second dielectric layer bonded to the bottom of said first dielectric layer to close the bottom of said crevice, said second dielectric layer having an aperture formed therein to define an opening at the bottom of said crevice;
   a bottom substrate bonded to the bottom of said second dielectric layer;
   means for measuring the temperature at said bottom substrate located on said bottom substrate; and
   a pair of electrodes located on the top of said bottom substrate, each of said electrodes having one end thereof located in said aperture for passing a current therethrough to measure the conductivity of the corrodents therein.

9. A conductivity sensor for use in a steam turbine in operation to monitor corrodents deposited therein, comprising:
   a bottom substrate;
   an electrode pair located on the top of said bottom substrate;
   a means for measuring the temperature at said bottom substrate located on said bottom substrate;
   a first layer of dielectric material bonded to the top of said bottom substrate, said first layer having an aperture formed therein such that an end of each of the electrodes of said electrode pair is located in said aperture;

a second layer of dielectric material bonded to the top of said first layer, said second layer defining a crevice for entrapping corrodents, a portion of the bottom of said crevice including said aperture so that a current may be passed between the ends of the electrodes of said electrode pair in said aperture to measure the conductivity of the corrodents therein; and a top substrate bonded to the top of said second layer.

10. The sensor of claim 9 including a second electrode pair located on the top of said bottom substrate, a second aperture formed in said first layer such that an end of each of the electrodes of said second electrode pair is located in said second aperture, and a portion of the bottom of said crevice including said second aperture so that a current may be passed between the ends of the electrodes of said second electrode pair in said second aperture to measure the conductivity of the corrodents therein.

11. The sensor of claims 9 or 10 wherein said top and bottom substrates are constructed of alumina.

12. The sensor of claim 11 wherein the electrodes are defined by a platinum-gold conductor path.

13. The sensor of claim 12 wherein said temperature measuring means is defined by a platinum-gold conductor path.

14. The sensor of claim 13 including terminal means located on said bottom substrate for connecting the electrodes and said temperature measuring means to a means for receiving signals therefrom and to a source of electrical power.

15. The sensor of claim 14 in which the electrodes are connected to a switching means for alternately reversing the polarity thereof.

16. The sensor of claim 15 in which a telemetry system is used to transmit power to and receive signals from the electrodes and said temperature measuring means.

17. A conductivity sensor for use in a steam turbine in operation to monitor steam-transported corrodents being deposited therein, comprising:
a bottom substrate;
a first electrode pair formed on the top of said bottom substrate;
a second electrode pair spaced from said first electrode pair and formed on the top of said bottom substrate;
a means for measuring the temperature at said bottom substrate located on said bottom substrate;
a first layer of dielectric material formed on the top of said bottom substrate so that said first and second electrode pairs and said temperature measuring means are located therebetween each separated from the other by the dielectric material of said first layer, said first layer having a first and second aperture formed therein such that an end of said first electrode pair is located in said first aperture and an end of said second electrode pair is located in said second aperture;
a second layer of dielectric material formed on the top of said first layer, said second layer defining a crevice therein for entrapping corrodents, a portion of the bottom of said crevice including said first and second apertures so that a current may be passed between the ends of said first and second electrode pairs located in said first and second apertures to measure the conductivity of the corrodents therein;

a top substrate formed on the top of said second layer; and terminal means on said bottom substrate for connecting said first and second electrode pairs and said temperature measuring means to a means for receiving signals therefrom and to a source of electrical power.

18. The sensor of claim 17 in which said first and second electrode pairs are connected to the source of electric power through a switching means for alternating the polarity of the electrodes thereof.

19. The sensor of claim 17 in which said bottom and top substrates are made of a material that can withstand the high pressures and temperatures present during operation of the turbine.

20. The sensor of claim 19 in which said first and second layers are made of a material that can withstand the high pressures and temperatures present during the operation of the turbine.

21. A conductivity sensor for use in a steam turbine to monitor steam-transported corrodents deposited on the turbine blades during operation of the turbine, comprising:
a first alumina substrate;
a pair of electrodes formed on the top of said first substrate;
a means for measuring the temperature of said first substrate located on said first substrate;
a first layer of dielectric material formed on the top of said first substrate wherein said electrodes and said temperature measuring means are each electrically insulated from the other by the dielectric material of said first layer, said first layer having an opening therein extending from the top to the bottom thereof so that an end of each of said electrodes is located therein;
a second layer of dielectric material formed on the top of said first layer, said second layer defining a crevice extending longitudinally thereof to entrap corrodents therein in which said opening in said first layer defines a portion of the bottom of said crevice so that a current may pass between the ends of said electrodes located in said opening to measure the conductivity of the corrodents deposited therein;
a second alumina substrate formed on the top of said second layer to close the upper portion of said crevice; and
terminals for said electrodes and said temperature measuring means located on said first substrate for connecting said electrodes and said temperature measuring means to a means for receiving signals therefrom and to a source of electrical power.

22. The sensor of claim 21 in which said first and second layers and said first and second substrates are substantially rectangular in shape.

23. The sensor of claim 22 in which said first substrate is longer than said second substrate and said first and second layers.

24. The sensor of claim 23 in which said second substrate and said first and second layers are of equal length, all of said substrates and said layers formed to be aligned at one end thereof so that the opposite end of said first substrate extends beyond the opposite ends of said second substrate and said first and second layers, said terminals being located on said first substrate at this end.

25. The sensor of claim 21 in which a telemetry system is used to transmit power to and receive signals from said electrodes and said temperature measuring means.

26. The sensor of claim 25 in which a signal cable of said telemetry system is connected at said terminals.

27. A method of constructing a conductivity sensor for use in a steam turbine in operation to monitor corrodents deposited therein, comprising:
   locating an electrode pair on the top of a first substrate;
   locating a means for measuring the temperature at said first substrate on said first substrate;
   forming a first layer of dielectric material on the top of said first substrate so that said electrode pair and said temperature measuring means are located therebetween;
   forming an aperture in said first layer so that an end of said electrode pair is located in said aperture;
   forming a crevice in a second layer of dielectric material for entrapping corrodents therein;
   forming said second layer on said first layer so that a portion of the bottom of said crevice includes said aperture so that a current may be passed across the end of said electrode pair in said aperture to measure the conductivity of the corrodents therein; and
   forming a second substrate on the top of said second layer to close the top of said crevice.

28. The method of claim 27 in which said temperature measuring means and said electrode pair are separated from each other by the dielectric material of said first layer.

29. The method of claim 28 in which said first and second substrates are made of alumina.

30. The method of claim 29 in which a platinum-gold paste is applied to said first substrate to form said electrode pair and said temperature measuring means.

31. The method of claim 27 further including transmitting electrical power to said electrode pair and said temperature measuring means and receiving signals therefrom by means of a telemetry system.

32. The method of claim 27 further including alternately reversing the polarity of the electrodes of said electrode pair to prevent decay thereof.

33. A method of constructing a conductivity sensor for use in a steam turbine in operation to monitor corrodents deposited therein, comprising:
   silk-screening an electrode pair and a RTD on the top of a first substrate;
   thermally fusing said electrode pair and said RTD to said first substrate;
   silk-screening a first layer of dielectric material to form an aperture therein;
   thermally fusing said first layer to the top of said first substrate so that said electrode pair and said temperature measuring means are located therebetween with an end of said electrode pair located in said aperture;
   silk-screening a second layer of dielectric material to form a crevice therein for entrapping corrodents;
   thermally fusing said second layer to said first layer so that a portion of the bottom of said crevice includes said aperture so that a current may be passed across the end of said electrode pair in said aperture to measure the conductivity of the corrodents therein; and
   thermally fusing a second substrate to the top of said second layer to close the top of said crevice.

34. The method of claim 33 wherein a second aperture is silk-screened into said first layer and a second electrode pair is silk-screened and thermally fused to said first substrate so that an end of said second electrode pair is located within said second aperture to measure the conductivity of the corrodents therein.

* * * * *